US005941855A

United States Patent [19]

Picha et al.

[11] Patent Number: 5,941,855

[45] Date of Patent: Aug. 24, 1999

[54] GASTROSTOMY DEVICE PACKAGE AND METHOD OF ASSEMBLY

[75] Inventors: George J. Picha, Independence; Gary Austin, Euclid, both of Ohio; Todd Snow, Westborough, Mass.

[73] Assignees: Applied Medical Technology, Inc., Cleveland, Ohio; Boston Scientific Corporation, Natick, Mass.

[21] Appl. No.: 08/943,900

[22] Filed: Oct. 3, 1997

[51] Int. Cl.[6] ..................... A61M 5/32

[52] U.S. Cl. ..................... 604/174; 604/523; 604/910; 604/500; 604/93

[58] Field of Search ..................... 604/174, 164, 604/170, 104, 106, 264, 280, 283, 910, 49, 54, 175, 93, 523, 500, 502; 128/DIG. 26

[56] References Cited

U.S. PATENT DOCUMENTS

| | | | |
|---|---|---|---|
| 3,951,153 | 4/1976 | Leucci . | |
| 4,059,111 | 11/1977 | Erasmus . | |
| 4,315,509 | 2/1982 | Smit . | |
| 4,315,513 | 2/1982 | Nawash et al. . | |
| 4,393,873 | 7/1983 | Nawash et al. . | |
| 4,516,578 | 5/1985 | Shuffield | 128/341 |
| 4,629,459 | 12/1986 | Ionescu et al. . | |
| 4,701,163 | 10/1987 | Parks . | |
| 4,732,152 | 3/1988 | Wallsten et al. . | |
| 4,758,219 | 7/1988 | Sacks et al. . | |
| 4,762,519 | 8/1988 | Frimberger . | |
| 4,798,592 | 1/1989 | Parks . | |
| 4,826,481 | 5/1989 | Sacks et al. . | |
| 4,878,906 | 11/1989 | Lindemann et al. . | |
| 4,913,141 | 4/1990 | Hillstead . | |
| 4,922,905 | 5/1990 | Strecker . | |
| 5,007,900 | 4/1991 | Picha et al. . | |
| 5,073,166 | 12/1991 | Parks et al. . | |
| 5,074,846 | 12/1991 | Clegg et al. . | |
| 5,080,650 | 1/1992 | Hirsch et al. | 604/104 |
| 5,084,014 | 1/1992 | Picha et al. . | |
| 5,100,384 | 3/1992 | McBrien et al. . | |
| 5,112,310 | 5/1992 | Grobe . | |
| 5,147,400 | 9/1992 | Kaplan et al. . | |
| 5,167,627 | 12/1992 | Clegg et al. | 604/101 |
| 5,234,454 | 8/1993 | Bangs | 606/191 |
| 5,234,456 | 8/1993 | Silvestrini . | |
| 5,267,969 | 12/1993 | Hirsch et al. . | |
| 5,273,529 | 12/1993 | Idowu . | |
| 5,391,159 | 2/1995 | Hirsch et al. | 604/268 |
| 5,405,378 | 4/1995 | Strecker . | |
| 5,476,505 | 12/1995 | Limon . | |
| 5,545,141 | 8/1996 | Eld | 604/164 |
| 5,555,898 | 9/1996 | Suzuki et al. . | |
| 5,628,753 | 5/1997 | Cracauer et al. | 606/108 |
| 5,807,314 | 9/1998 | Ross et al. | 604/49 |

*Primary Examiner*—Corrine McDermott
*Assistant Examiner*—Cris L. Rodriguez
*Attorney, Agent, or Firm*—Pearne, Gordon, McCoy & Granger LLP

[57] ABSTRACT

A gastrostomy device having a tubular portion, first and second fingers, a rod member, and a suture member. The rod member and suture member cooperate to releasably retain the fingers in a first or installation configuration for insertion through a patient's stoma. Following insertion, the rod member and suture member release the fingers to permit the fingers to move to a deployed configuration. In the installation configuration the fingers are generally in line with an axis of the tubular portion while, in the deployed configuration, the fingers are generally transverse to the tubular portion axis.

15 Claims, 5 Drawing Sheets

Fig.3
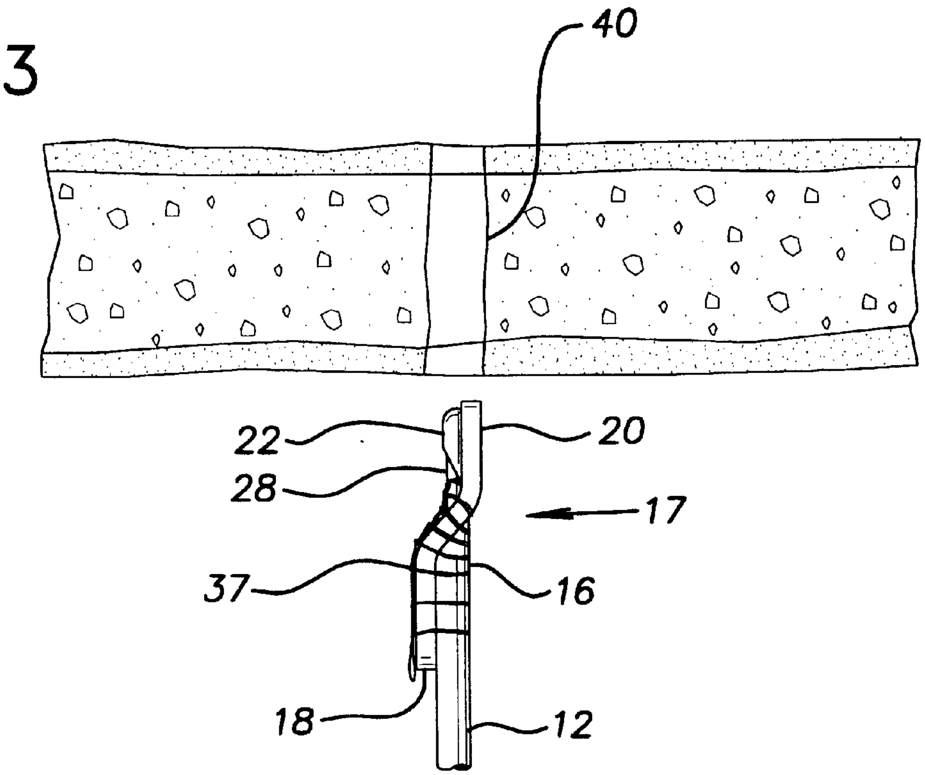
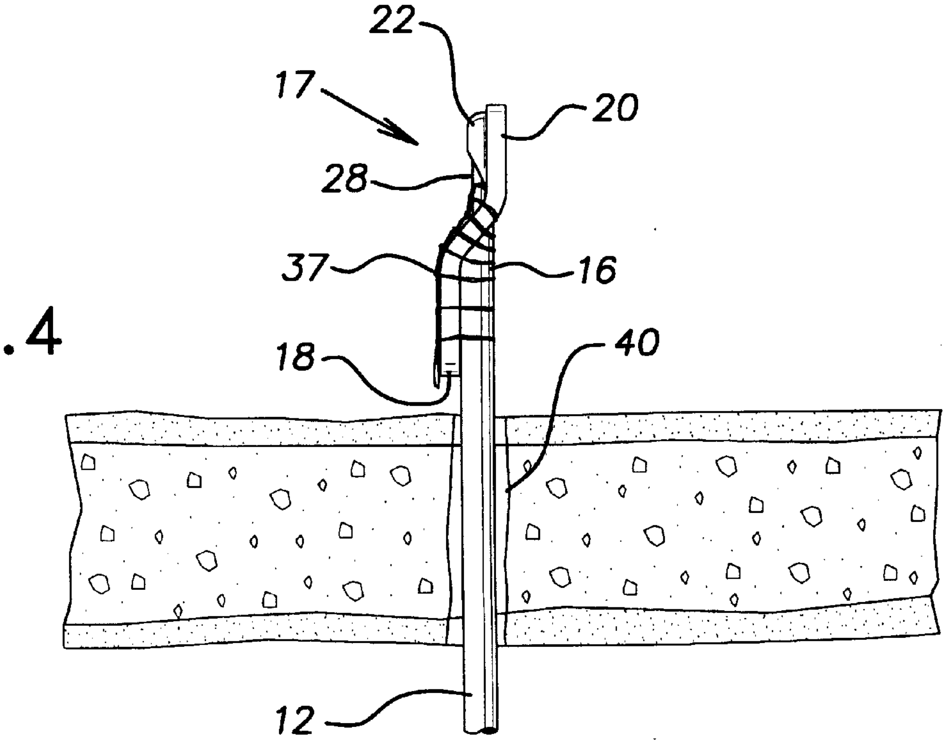
Fig.4

GASTROSTOMY DEVICE PACKAGE AND METHOD OF ASSEMBLY

BACKGROUND OF THE INVENTION

The present invention is directed toward a percutaneous gastrostomy device and toward a method for installing a gastrostomy device within a patient.

Several different gastrostomy device designs have been developed and employed over the years. Each of these designs has met with varying degrees of success. U.S. Pat. No. 5,007,900, the disclosure of which is expressly incorporated herein in its entirety, discloses one type of gastrostomy device that has been well received in recent years. The '900 device includes a resilient tube having a distal end with a resilient retainer. The retainer has a pocket radially spaced from the tube and adapted to receive a rod and permit proper orientation of the retainer. More specifically, the rod urges the retainer to a stretched position collateral with the tube to facilitate installation of the gastrostomy device within a patient.

U.S. Pat. Nos. 4,311,148 and 4,668,225 show feeding tubes or catheters having resilient wing-like protrusions about the end of the tube for retaining the tubes within a passage through the wall of a body cavity. The tubes are designed to be inserted into the patient through fresh incisions that are then sutured about the tube. To remove these tubes from the cavity, it is possible to pull the end through the passage while exerting sufficient force to fold the wings back out of the way.

U.S. Pat. No. 4,573,576 shows a catheter with a disk-like retainer on one end. A line is introduced through an incision in the patient's skin, fascia and stomach wall, and an endoscope is used to capture the loose end within the stomach and to draw it out the patient's mouth. The line is then used to draw the tube portion of the catheter out through the incision. An endoscope is also used to remove the catheter.

After an incision establishes a passage through the body wall and a tube is passed therethrough, over a period of time, the body heals to a degree about the tube thereby forming a stoma. The passage or stoma becomes relatively stable, much like the hole for pierced ears, for example. Without the tube, the stoma would eventually close up, but in the meantime, a well-defined passage exists, even if the tube is withdrawn.

This well-defined passage is suitable for the external percutaneous insertion of appropriately designed catheters. However, none of the aforementioned gastrostomy devices are suitable for this purpose, largely because of the difficulty in pushing a flexible tube, versus pulling it, and also because the folded-over wings make a poor dilator for the passage.

U.S. Pat. No. 4,863,438, which is included herein in its entirety by reference, shows a catheter that may be inserted into the stoma from outside the body. A hollow mushroom-shaped resilient head on the tube may be distended by the insertion of a rigid obturator into the tube, the distended head acting as a dilator small enough to pass through the stoma. Once the head clears the stoma, the obturator is withdrawn, and the head expands. A similar process is employed to remove this device, or mechanical traction may be used to remove the device.

U.S. Pat. No. 5,405,378, the disclosure of which is expressly incorporated herein in its entirety, discloses a flexible probe and a tubular element that fits over the probe. The tubular element is retained by a filament wound around the outer periphery of the element. The tubular element is retained on the outer periphery of the probe in a radially-impressed state. Upon appropriate placement of the element in a blood vessel, the filament is pulled to release the element and enable the element to expand into place.

The known methods and devices for placement of gastrostomy tubes require several steps and significant difficulty for the surgeon, thereby increasing the time and expense of the procedure. Therefore, there exists a need in the art for a gastrostomy tube which is easily installed, and definitely secured to the patient.

SUMMARY OF THE INVENTION

The present invention is directed toward a gastrostomy device which is easy to install within a patient and which is readily converted from a first or installation orientation to a second or deployed orientation. The present invention is also directed toward a method for installing a gastrostomy device within a patient.

In accordance with the present invention, a gastrostomy device includes a tubular portion having an inner end and an outer end. An internal bolster comprising first and second fingers is secured to the inner end of the tubular portion. The first and second fingers extend laterally from the inner end of the tubular portion. The fingers are oriented in either the first, installation orientation or the second, deployed orientation. In the first orientation the fingers are generally in-line with an axis of the tubular portion to facilitate insertion of the device via a stoma. In the deployed orientation the fingers are generally transverse to the tubular portion axis and thereby prevent removal of the device.

In further accordance with the present invention a rod member extends through the tubular portion and has an end which projects from the tubular portion intermediate the fingers. The projecting end of the rod member is received within a pocket provided by the first finger. A suture member extends through the rod member and includes a first portion and a second portion. The first portion projects from the rod member and the outer end of the tubular portion. The second portion projects from the rod member projecting end and the inner end, and binds the second finger to the tubular portion.

BRIEF DESCRIPTION OF THE DRAWINGS

These and further features of the present invention will be apparent with reference to the following description and drawings wherein:

FIGS. 3–5 illustrate installation of the gastrostomy device shown in FIGS. 1–2 within a patient;

DETAILED DESCRIPTION OF THE PREFERRED EMBODIMENTS

Figures 1, 2:
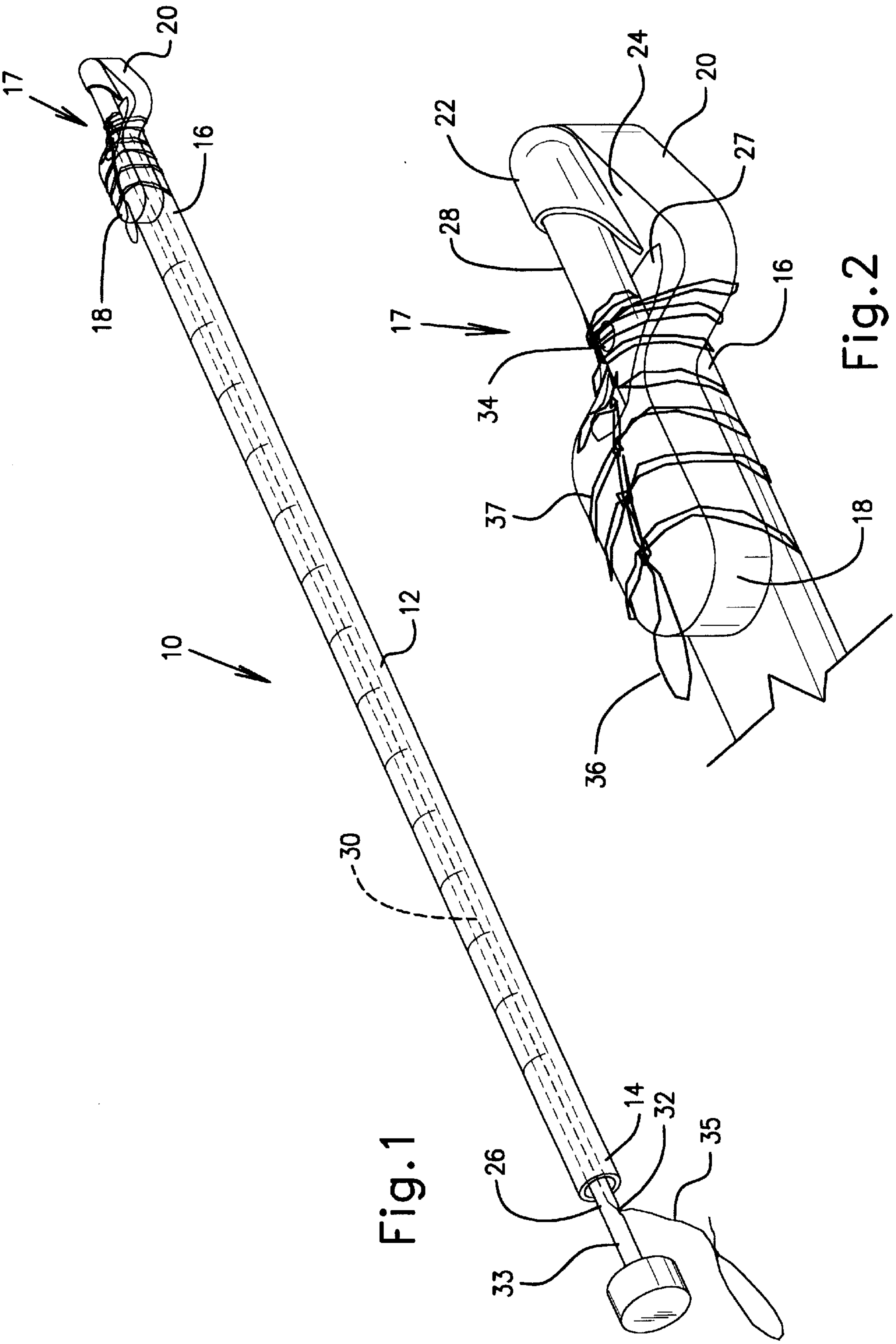
FIG. 1 is a perspective view of a gastrostomy device according to the present invention.
FIG. 2 is an enlarged perspective view of an end portion of the gastrostomy device shown in FIG. 1.

With reference to the drawing figures, a gastrostomy device and method of installation is illustrated. The gastrostomy device 10 includes a tubular portion 12 having an outer end 14 and an inner end 16. The inner end 16 has an internal bolster 17 comprising first and second oppositely-extending fingers 18, 20 secured thereto. Preferably, the tubular portion 12 and the internal bolster 17 are integrally molded together from a biocompatible material, such as silicone plastic. The fingers 18, 20 normally extend generally transverse to a length direction of the tubular portion 12. The second finger 20 has a pocket 22 formed on an outer surface 24 thereof. The pocket 22 is adapted to receive a portion of a rod member 26, as will be discussed more fully hereinafter.

The rod member 26 slidably extends through the tubular portion 12 and projects out of an opening 27 at the inner end 16. The opening 27 is generally intermediate the fingers 18, 20. A projecting end 28 of the rod member 26 is inserted into the pocket 22 provided by the second finger 20. The rod member 26 is preferably hollow, or has a longitudinal passage, to accommodate a suture member or thread 30.

A first hole or opening 32 is formed in the side wall of the rod member 26 at the outer end 33 thereof. A second opening 34 is formed in the projecting end 28 of the rod member 26. The openings 32, 34 communicate with the hollow interior of the rod member 26 and cooperate with the rod member hollow interior to define a passageway through which the suture or thread 30 extends. Alternatively, the first opening may be formed in an end cap on the rod member 26. In this alternative, the end cap first opening is in communication with the hollow interior of the rod member and the suture member extends therethrough.

The suture member or thread 30 cooperates with the rod member 26 to provide a secure yet easily removable restraint for the first and second fingers 18, 20, and thereby permits facile installation of the gastrostomy device 10 within the body of the patient, as will be discussed more fully hereinafter with particular reference to FIGS. 3–5. To that end, a first portion 35 of the suture member projects from the tubular portion outer end 14 and a second portion 36 of the suture member 30 projects from the tubular portion inner end 16. More specifically, the suture member 30 extends through the rod member 26 and the first portion 35 projects from the first opening 32 while the second portion 36 projects from the second opening 34, as illustrated.

The second portion 36 of the suture member 30 is configured as a suture wrap 37 that is wound around the first finger 18 in a multiple slip-knot type configuration. The first portion 35 of the suture member 30 may include a pull tab (not shown) to facilitate grasping and pulling thereof.

As such, pulling of the first portion 35 of the suture member 30 relatively away from the suture wrap 37 causes the suture wrap 37 to unravel. The suture wrap 37 releasably binds or holds the first finger 18 against the tubular portion 12. The second finger 20 is held away from the tubular portion 12 by the rod member 26. The suture wrap 37 and rod member 26 cooperate to stretch and deform the fingers 18, 20 from their normal or second orientation transverse to the axis of the tubular portion 12 to the installation orientation generally aligned with the axis of the tubular portion 12 and the rod member 26, as shown in FIGS. 1–2.

The second portion 36 of the suture member 30 is wrapped around the first finger 18 such that pulling the first portion 35 of the suture member to move the suture member 30 through the rod member 26 causes the suture wrap 37 to unravel and thereby release the first finger 18 from the tubular portion 12. Thereafter, the rod member 26 may be pulled or withdrawn through the tubular portion 12 to remove the rod member projecting end 28 from the second finger pocket 22 and thereby permit the first and second fingers 18, 20 to move from the first position or orientation generally in line with the tubular portion 12 to the second position or orientation generally transverse to the tubular portion 12.

Alternatively, removal of the rod member 26 from the tubular portion 12 will both withdraw the rod member projecting end 28 from the second finger pocket 22 and pull the suture member 30 through the tubular portion to cause the suture wrap 37 to unravel release the first finger 18. Thus, in the contemplated alternative only one operative step is required release the first and second fingers 18, 20 and permit them to move from the first orientation to the second orientation.

Naturally, it is considered apparent that the exact method or type of releasable suture wrap 37 shown and described herein is exemplary in nature insofar as one skilled in the art will be able to use and develop numerous suture wrap patterns equivalent to the present without departing from the scope and spirit of the present invention. Therefore, the present invention covers and includes each of the numerous equivalent ways in which the internal bolster 17 may be wrapped.

Figure 5:
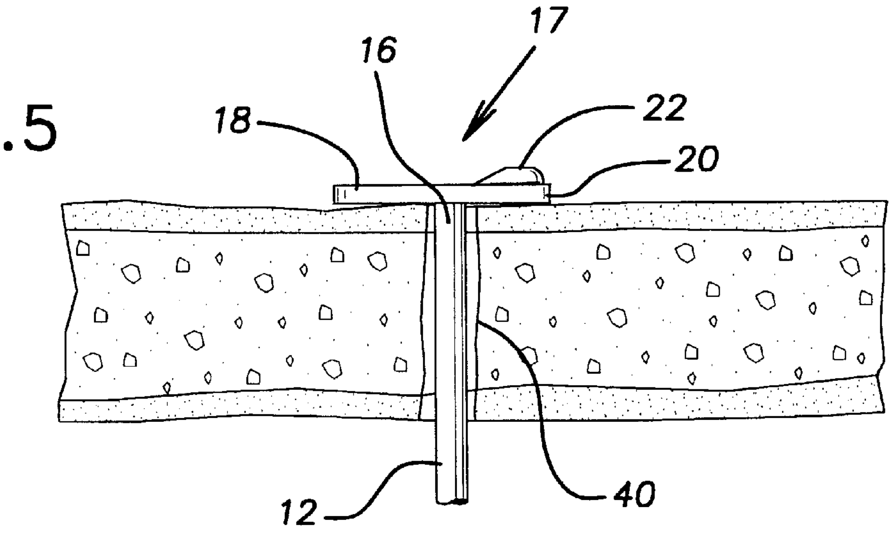

Turning to FIGS. 3–5, a method of installing the gastrostomy device 10 according to the present invention within a patient is illustrated. The gastrostomy device 10, with suture wrap 37 in place as shown in FIG. 1, is aligned with and inserted through the patient's stoma 40. The suture wrap 37 and rod member 26 cooperate to maintain the fingers 18, 20 in the first or installation orientation to reduce the profile of the gastrostomy device internal bolster 17 and ease insertion of same through the stoma 40.

Once the internal bolster 17 of the gastrostomy device 10 is within the interior of the patient, as shown in FIG. 4, the first portion 35 of the suture member is pulled to withdraw the suture member 30 from the rod member 26 and unravel the suture wrap 37 to release the first finger 18. The rod member 26 is then pulled out of the tubular portion 12 and the pocket 22 to release the second finger 20. Once released, the first and second fingers 18, 20 move from the first orientation to the deployed or second orientation and serve to prevent unintended withdrawal of the internal bolster 17 from via the stoma 40. The gastrostomy device 10 is then generally as shown in FIG. 5. Thereafter, an external bolster (not shown) may be attached to the tubular portion 12 adjacent the patient's skin surface to prevent the gastrostomy device 10 from being inadvertently pushed into the patient's body. Numerous types of known external bolsters are suitable for use with the present invention, and are therefore not further described herein. The inclusion of scale indicia on the tubular portion 12 permits easy measuring of the patient's body wall thickness, which may be helpful for replacement purposes.

With reference to FIGS. 6–12, an alternative embodiment of the gastrostomy device 110 is illustrated. The illustrated alternative is the subject of co-pending U.S. patent application Ser. No. 09/052,167, (Pearne, Gordon Docket No. 30168) the disclosure of which is expressly incorporated herein in its entirety. The alternative embodiment varies from that shown in FIGS. 1–5 primarily by providing a different internal bolster 117, with the tubular portion 12, the rod member 26, and the method of installation being generally identical to that previously discussed. In the following description of the alternative embodiment, identical reference numerals are used to refer to structural elements common to both embodiments.

With reference to FIGS. 8–12, the internal bolster 117 is shown to be generally symmetrical about a center line A—A, and defines an inner surface 120 and an outer surface 122. The inner surface 120 faces toward the tubular portion 12 and is curved to a slightly convex shape. The curvature or radius of the inner surface is generally constant as one moves outwardly from the tubular portion 12 toward a peripheral edge 123 of the internal bolster 117, as illustrated.

The outer surface 122 faces away from the tubular portion 12 and includes an inner oval-shaped portion 124 and a surrounding portion 126. The inner oval portion 124 is oriented generally transverse to the center line A—A, as illustrated. The outer surface 122 at the inner oval portion 124 is generally planar, while the surrounding portion 126 is slightly curved and generally matches the curvature of the inner surface 120. Accordingly, the outer surface 122 provides a generally flat-bottomed, concave or bowl-like shape. Due to the differing shapes of the inner and outer surfaces 120,122, the internal bolster 117 has a varying thickness, with the radially inner portion coinciding with the inner oval portion 124 being relatively thicker than the remaining portion of the internal bolster (corresponding to the surrounding portion 126).

Accordingly, the area immediately surrounding the tubular portion 12 is relatively less flexible than the remaining portion of the internal bolster 117, which aides in reconfiguring the internal bolster between the deployed and installation configurations, and provides desirable internal bolster resistance to withdrawal forces. Moreover, the relatively increased resistance to flexing provided by the increased thickness at the inner oval portion 124 is directed transverse to the center line or length of the internal bolster 117 and tends to resist flexing or folding of lateral regions 130 of the internal bolster 117 toward the center line A—A thereof.

The internal bolster 117 has a first part 132 and a second part 134, each of which are bisected by the center line A—A. The first and second parts 132,134 cooperate to provide the aforementioned lateral regions 130. The lateral regions 130 are secured in a deformed condition when the internal bolster 117 is in an installation configuration, as will be discussed more fully hereinafter.

The first part 132 of the internal bolster 117 is generally semi-oval. The second part 134 of the bolster is integrally connected to the first part and defines a tab-like member 136. The tab-like member 136 includes, on its outer surface, a pocket 138 for receipt of the rod member 26 to permit deformation of the internal bolster 117 from a deployed configuration (FIGS. 8–12) to an installation configuration (FIGS. 6–7), as will be discussed more fully hereinafter.

Figure 6:
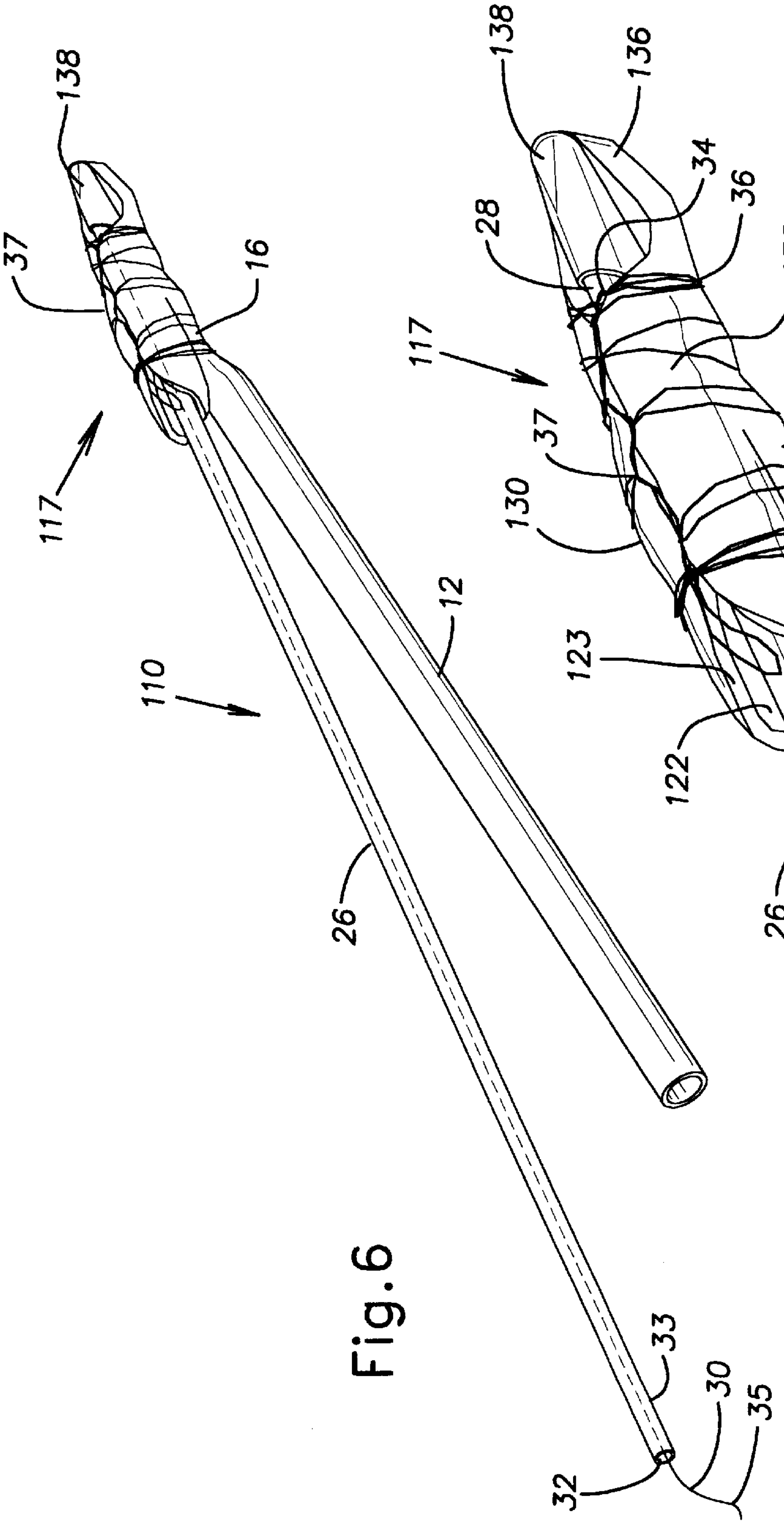
FIG. 6 is a perspective view of a gastrostomy according to an alternative embodiment.
Figure 7:
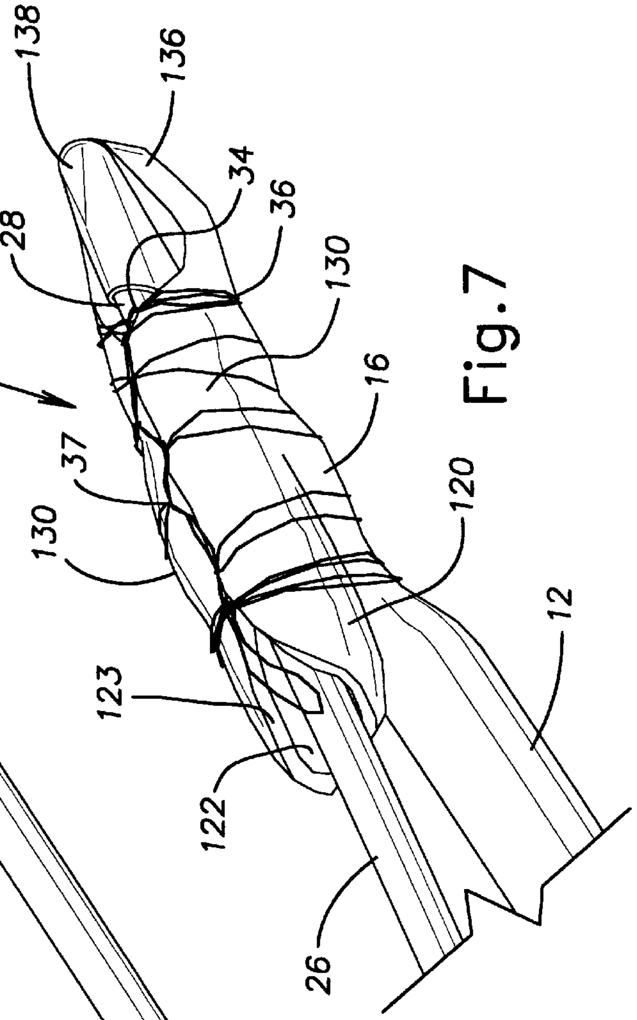
FIG. 7 is an enlarged perspective view of an alternative internal bolster, shown in an installation configuration.

With specific reference to FIGS. 6–7, the rod member 26 preferably extends alongside and generally parallel to the tubular portion 12 and includes the projecting end 28 that extends beyond the tubular portion opening 27 (FIGS. 8–9) at the inner end 16 thereof. The rod member projecting end 28 is removably inserted into the pocket 138 provided by the second part 134 of the internal bolster 117. As such, the second part 134 of the internal bolster 117 is bent or deformed by the rod member 26 to be generally in-line with an axis of the tubular portion 12, as illustrated.

As in the aforementioned first embodiment, the rod member 26 is preferably hollow to accommodate a suture or 30 thread that extends therethrough. A first hole or opening 32 is formed in the outer end 33 of the rod member. A second opening 34 is formed in the projecting end 28 of the rod member 26. The first and second openings 32,34 communicate with the hollow interior of the rod member 26 and define a passageway through which the suture member 30 extends. Alternatively, the first opening 33 may be formed in the sidewall of the rod member 26, or in a circular end cap on the rod member 26, as noted hereinbefore.

Figure 9:
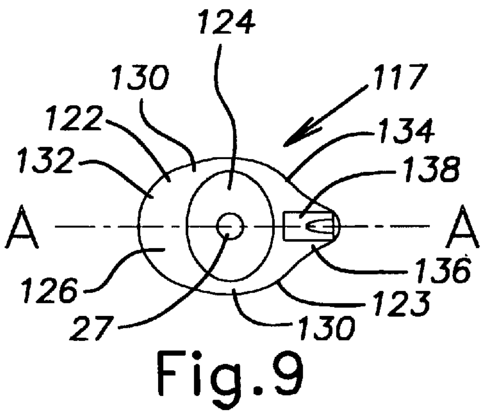
FIG. 9 is a top plan view of the internal bolster shown in FIG. 8.
Figure 8:
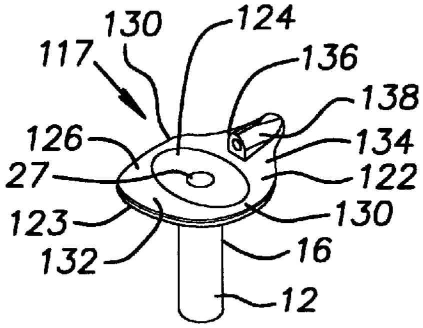
FIG. 8 is a perspective view of the internal bolster shown in FIG. 7 in a deployed configuration.
Figure 11:
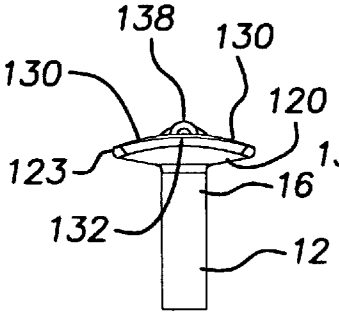
FIG. 11 is a left end elevational view of the internal bolster shown in FIGS. 8–10; and, FIG. 12 is a left end elevational view of the internal bolster shown in FIGS. 8–11.
Figure 10:
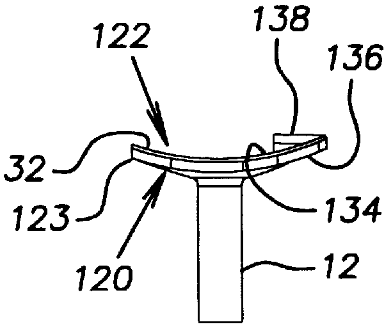
FIG. 10 is a front side elevational view of the internal bolster shown in FIGS. 8–9.
Figure 12:
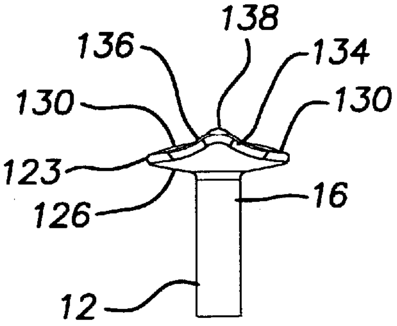

The suture member 30 cooperates with the rod member 26 to provide a secure yet easily removable restraint for the internal bolster 117 and thereby permits facile installation of the alternative gastrostomy device within the body of the patient, as will be discussed more fully hereinafter with particular reference to FIGS. 9–11. To that end, the first portion 35 of the suture member 30 projects from the rod member outer end 33 and the second portion 36 of the suture member 30 projects from the rod member projecting end 28. More specifically, the suture member 30 extends through the rod member 26 and the first portion projects 35 from the first opening 32 while the second portion 36 projects from the second opening 34, as illustrated.

The second portion 36 of the suture member 30 is configured as a suture wrap 37 that is wound around the first part 132 of the internal bolster 117 and the inner end 16 of the tubular portion 12 in a multiple slip-knot type configuration. As should be apparent from the drawings, the lateral regions 130 of the internal bolster 117 are folded, generally about the center line A—A, and about the rod member 26 and are retained in the folded position by the suture wrap 37. The peripheral edge 123 of the lateral regions 130 are adjacent one another, as illustrated, but may in some cases abut or slightly overlap. The first portion 35 of the suture member 30 may include a pull tab (not shown) to facilitate grasping and pulling thereof.

Pulling the first portion 35 of the suture member 30 relatively away from the suture wrap 37 causes the suture wrap, which releasably binds or holds the first part 132 of the internal bolster 117 against the tubular portion inner end 16, to unravel. The second part 134 of the internal bolster 117 is held away from the tubular portion 112 by the rod member 26. The suture wrap 37 and rod member 26 thus cooperate to stretch and deform the first and second parts 132,134 of the internal bolster 117 from their normal or second configuration transverse to the axis of the tubular portion (FIGS. 8–12) to the installation configuration generally aligned with the axis of the tubular portion 12 and the rod member 26 (FIGS. 6–7).

As discussed previously with respect to the first embodiment, the second portion 36 of the suture member 30 is wrapped around the first part 132 of the internal bolster 117 such that pulling the first portion 35 of the suture member 30 to move the suture member through the rod member 26 causes the suture wrap 37 to unravel and thereby release the first part 132 of the internal bolster 117 from the tubular portion inner end 16. Thereafter, the rod member 26 may be pulled or withdrawn to remove the 28 rod member projecting end from the pocket and thereby permit the internal bolster 117 to move from the first position or installation configuration generally in line with the tubular portion 12 to the second position or deployed configuration generally transverse to the tubular portion 12.

Alternatively, and as noted hereinbefore, it is contemplated that pulling the rod member 26 will both (either simultaneously or sequentially) withdraw the rod member projecting end 28 from the pocket 138 to release the second part 134 of the internal bolster 117 and pull the suture member 30 to cause the suture wrap 37 to unravel and release the first part 132 of the internal bolster 117. As such, in the contemplated alternative, only one operative step is required release the first and second parts 132, 134 of the internal bolster 117 and permit the bolster to move from the first or installation configuration to the second or deployed configuration.

Naturally, in the alternative embodiment it is also considered apparent that the exact method or type of releasable suture wrap shown and described herein is exemplary in nature insofar as one skilled in the art will be able to use and develop numerous suture wrap patterns equivalent to the present without departing from the scope and spirit of the present invention. Therefore, the present invention covers and includes each of the numerous equivalent ways in which the internal bolster may be wrapped.

It is further considered apparent that the rod member 26 may extend through the tubular portion 12 instead of alongside same. However, having the rod member external to the tubular portion permits the tubular portion to be radially compressed by the suture wrap and may, therefore, help minimize the profile of the alternative gastrostomy device presented for insertion into the patient's stoma.

The alternative gastrostomy device, with suture wrap 37 in place as described above, is aligned with and inserted through the patient's stoma. The suture wrap 37 and rod member 26 cooperate to maintain the bolster 117 in an undeployed or installation configuration to reduce the profile of the alternative gastrostomy device presented for insertion, and thereby permits insertion of the internal bolster 117 through the stoma. In this regard, compression of the tubular portion inner end 16 by the suture wrap 37 assists in reducing the profile of the alternative gastrostomy device presented for insertion. Once the inner end of the device is within the interior of the patient, the first portion 35 of the suture member is pulled to cause the suture wrap 37 to unravel and release the internal bolster first part 132. Thereafter, the rod member 26 is pulled to withdraw the projecting end 28 from the pocket 138 and release the bolster second part 134. The bolster 117 and alternative gastrostomy device are thereafter in the deployed configuration.

Once the internal bolster 117 is in the deployed configuration, a clamp or exterior locking-type bolster may be attached to the tubular portion adjacent the patient's skin surface to prevent the alternative gastrostomy device from being pushed into the patient's body. The inclusion of scale indicia on the tubular portion 12 permits easy measuring of the patient's body wall thickness, which may be helpful for replacement purposes.

While the preferred embodiment of the present invention is shown and described herein, it is to be understood that the same is not so limited but shall cover and include any and all modifications thereof which fall within the purview of the invention.

What is claimed is:

1. A percutaneous gastrostomy device, comprising:

a tubular portion defining a longitudinal axis;

an internal bolster secured to said tubular portion, said internal bolster being flexible to permit elastic deformation between a first orientation generally aligned with said longitudinal axis and a second orientation generally transverse to said tubular portion longitudinal axis;

a suture member having a first portion and a second portion, said second portion being wrapped around said internal bolster to retain said internal bolster in said first orientation, wherein pulling of said first portion causes said second portion to unwrap from said internal bolster and thereby permit the internal bolster to move from said first orientation to said second orientation.

2. A percutaneous gastrostomy device, comprising:

a tubular portion having an inner end;

an internal bolster secured to said inner end, said bolster comprising first and second fingers, said second finger defining a pocket;

a rod member having a hollow interior and a projecting end, said projecting end having an opening formed therein, said rod member being removably received within said tubular portion and said projecting end being removably received within said pocket; and a suture member, said suture member extending through the hollow interior of said rod member, through said opening in the projecting end of said rod member, and being wrapped around said first finger, wherein said suture member secures said first finger to said tubular portion during installation of said device and is operable to release said first finger from said tubular portion.

3. The percutaneous gastrostomy device according to claim 2, wherein said suture member is pulled to release said first finger.

4. The percutaneous gastrostomy device according to claim 2, wherein said rod member is pulled relatively away from said tubular portion inner end to remove said projecting end from said pocket and to release said first finger from said tubular portion.

5. The percutaneous gastrostomy device according to claim 4, wherein pulling said rod member causes said suture member to unwrap from said first finger and thereby release said first finger from said tubular portion to permit said device to assume a deployed orientation wherein said fingers extend generally transverse to an axis of said tubular portion.

6. The percutaneous gastrostomy device according to claim 2, wherein said first and second fingers extend laterally from said inner end in a deployed orientation, said rod member and said suture member cooperating to maintain said fingers in an installation orientation, said fingers being relatively more in-line with an axis of said tubular portion when in said installation orientation than when in said deployed orientation.

7. The percutaneous gastrostomy device according to claim 6, wherein, when in said installation orientation, said first finger extends in a first direction and said second finger extends in a second direction, said first direction being generally opposite said second direction.

8. The percutaneous gastrostomy device according to claim 7, wherein said suture member is unwrapped from said first finger to permit said first finger to move from said installation orientation toward said deployed orientation.

9. The percutaneous gastrostomy device accordingly to claim 8, wherein removal of said rod member from said pocket permits said second finger to move from said installation orientation toward said deployed orientation.

10. The percutaneous gastrostomy device according to claim 6, wherein pulling said rod member relatively away from said tubular portion inner end removes said projecting end from said pocket and releases said second finger from said tubular portion.

11. The percutaneous gastrostomy device according to claim 10, wherein pulling said rod member causes said suture member to unwrap from said first finger and thereby releases said first finger from said tubular portion to permit said device to assume the deployed orientation wherein said fingers extend generally transverse to the axis of said tubular portion.

12. A method of assembling a percutaneous gastrostomy device, said device including a tubular portion, first and second fingers extending from said tubular portion, a retaining pocket formed in said second finger, a rod member, and a suture member, said rod member defining a hollow interior passage with first and second openings to said passage, comprising the steps of:

inserting said suture member through said rod member first opening, through the passage, and out of said second opening of said rod member such that a first portion of said suture member extends from said first opening and a second portion of said suture member extends from said second opening;

pushing said rod member through said tubular portion, said rod member having a projecting end which extends through an exit opening of said tubular portion intermediate said fingers;

inserting said projecting end into said pocket such that said second opening of said rod member is accessible and disposed between said pocket and said tubular portion;

wrapping said suture member second portion around said first finger and said tubular portion to releasably bind said first finger to said tubular portion.

13. The method according to claim 12, comprising the further step of stretching said second finger with said rod member while said suture member second portion is being wrapped around said first finger and said tubular portion.

14. A method of installing a percutaneous gastrostomy device within a patient, said device including a tubular portion with an inner end and an outer end, first and second fingers extending from said inner end, a rod member having a portion that is removably received within a pocket formed in said second finger, a suture member extending through said rod member and having a first portion while extends from said device and a second portion operable to releasably secure said first finger to said tubular portion, said suture member and said rod member cooperating to releasably retain said first and second fingers in an installation orientation, said method comprising the steps of:

positioning said device such that said inner end of said tubular portion is spaced inwardly of an interior surface of the patient;

releasing said suture member second portion from said first finger to permit said first finger to move relative to said tubular portion toward a deployed orientation; and, removing said rod member projecting end from said pocket to permit said second finger to move relative to said tubular portion toward said deployed orientation, said deployed orientation being generally transverse to an axis of said tubular portion.

15. The method according to claim 14, wherein said rod member is disposed within said tubular portion, comprising the further step of removing said rod member from said tubular portion.

* * * * *